United States Patent [19]

Horecker

[11] Patent Number: 4,696,915

[45] Date of Patent: Sep. 29, 1987

[54] PARATHYMOSIN ALPHA

[75] Inventor: Bernard L. Horecker, New York, N.Y.

[73] Assignee: Hoffmann-La Roche Inc., Nutley, N.J.

[21] Appl. No.: 794,273

[22] Filed: Nov. 4, 1985

Related U.S. Application Data

[63] Continuation of Ser. No. 614,007, May 25, 1984, abandoned.

[51] Int. Cl.[4] .................... C07K 15/12; A61K 35/26; A61K 37/24
[52] U.S. Cl. ........................ 514/21; 424/95; 530/301; 530/399
[58] Field of Search ............................ 514/21; 424/95; 530/301, 399

[56]  References Cited

U.S. PATENT DOCUMENTS 4,490,289  12/1984  Stern ............................... 260/112 R

OTHER PUBLICATIONS

Hackh's Chemical Dictionary, fourth ed., p. 326, "Homogeneity, Homogeneous".
IUPAC-IUB Joint Commission on Biochemical Nomenclature, 1983, pp. 11-37.
Goldstein et al., "Current Status of Thymosin . . . ", Recent Progress in Hormone Research, vol. 37, 1981, pp. 369-414.

Primary Examiner—J. R. Brown
Assistant Examiner—Jacqueline M. Stone
Attorney, Agent, or Firm—Jon S. Saxe; George M. Gould; Julie M. Prlina

[57]  ABSTRACT

Parathymyosin alpha is a novel peptide isolated from mammalian thymus and contains approximately 105 amino acid residues. It bears a high degree of homology to prothymosin alpha both in sequence and amino acid composition. Parathymosin alpha acts as a blocker or modulator or prothymosin alpha activity.

4 Claims, 3 Drawing Figures

PARATHYMOSIN ALPHA

This application is a continuation of application Ser. No. 614,007, filed 5/25/84, and now abandoned.

BACKGROUND OF THE INVENTION

A number of immunologically active peptides have been isolated from mammalian thymic extracts. Such thymic peptides include the structurally related thymosin alpha-1 thymosin alpha-11 and more recently prothymosin alpha. See in this regard U.S. patent application Ser. No. 546,211, filed Oct. 27, 1983. Prothymosin alpha, identified as a larger peptide containing the thymosin alpha-1 sequence at its amino-terminus, was shown to account for most, if not all, of the immunoreactivity detected with an antibody directed against the amino-terminal sequence of thymosin alpha-1. All the aforesaid thymosin alphas exhibit immuno-potentiating activity and are involved in the regulation, differentiation and function of T-cells.

SUMMARY OF THE INVENTION

It has now been found that a novel peptide which shows some structural homology to prothymosin alpha can be isolated from mammalian thymus, most particularly rat thymus. This novel peptide can also be isolated from other rat tissues in that it is surprisingly present in much higher concentrations in such tissues than in the thymus. Suitable tissue sources include for example, liver, kidney and brain. Parathymosin alpha contains approximately 105 amino acid residues and thus is of similar size to prothymosin alpha (112 amino acid residues). Similarities are also seen in the amino acid composition of this compound and prothymosin alpha. Most surprisingly, in spite of the indicated structural relationship between these compounds, parathymosin alpha appears to act as a blocker or modulator to the immunoenhancing activity exhibited by prothymosin alpha. Thus such immunomodulating activity would suggest its usefulness in treatment of auto-immune diseases. in establishing immuno-suppression such as needed for carrying out organ transplantation or to inhibit host-graph reactions.

DESCRIPTION OF THE PREFERRED EMBODIMENT

Parathymosin alpha is conveniently obtained by extraction of suitable mammalian tissue. For purpose of convenience and illustration, the isolation of parathymosin alpha from rat thymus is described herein. However, as pointed out above, other tissues are suitable substrates for such extraction in that parathymosin is found in lung, liver, kidney and brain at levels even higher than those found in the thymus gland.

Thus, fresh rat thymus was frozen in liquid nitrogen and pulverized in the frozen state. The powdered frozen tissue was quickly brought to 95°–100° C. in a relatively large volume of boiling 0.1M sodium phosphate buffer, pH 7.0 and kept at 95°–100° C. for 5 min. After cooling, the suspension was homogenized with a Polytron Homogenizer (Brinkmann) and the soluble fraction collected. The clear extracts were desalted on Sep-Pak C-18 cartridges (Waters Associates) and the peptides separated by chromatography on a column (Sephacryl S-200) and purified by reversed phase HPLC.

Figure 1:
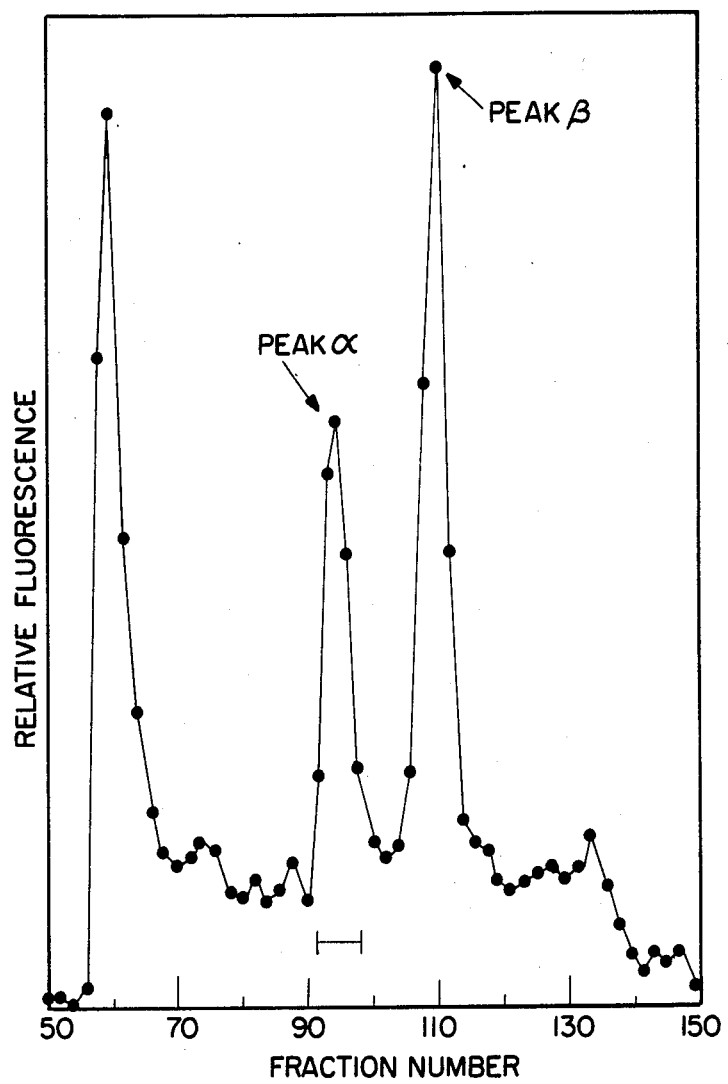

Chromatography of the desalted extracts on the Sephacryl S-200 yielded three peaks as seen in FIG. 1. The gel filtration on Sephacryl S-200 was carried out as follows. Aliquots (0.8 ml) of the lyophilized eluates from the Sep-Pak C-18 cartridges, dissolved in 1M formic acid/0.2M pyridine, pH 2.8 (buffer A), were applied to a Sephacryl S-200 (1.5×89 cm) column, previously equilabrated with buffer A. The column was developed with the same buffer at a flow rate of 8.5 ml/h and 0.85 ml fractions were collected. To locate peptide peaks, aliquots (10 ml) were dried, hydrolized with alkali and analyzed with fluorescamine. For subsequent purification by HPLC, the fractions corresponding to peak alpha as indicated by the bar in FIG. 1 were pooled and combined with similar fractions from 3 other gel filtration separations.

Figure 2:
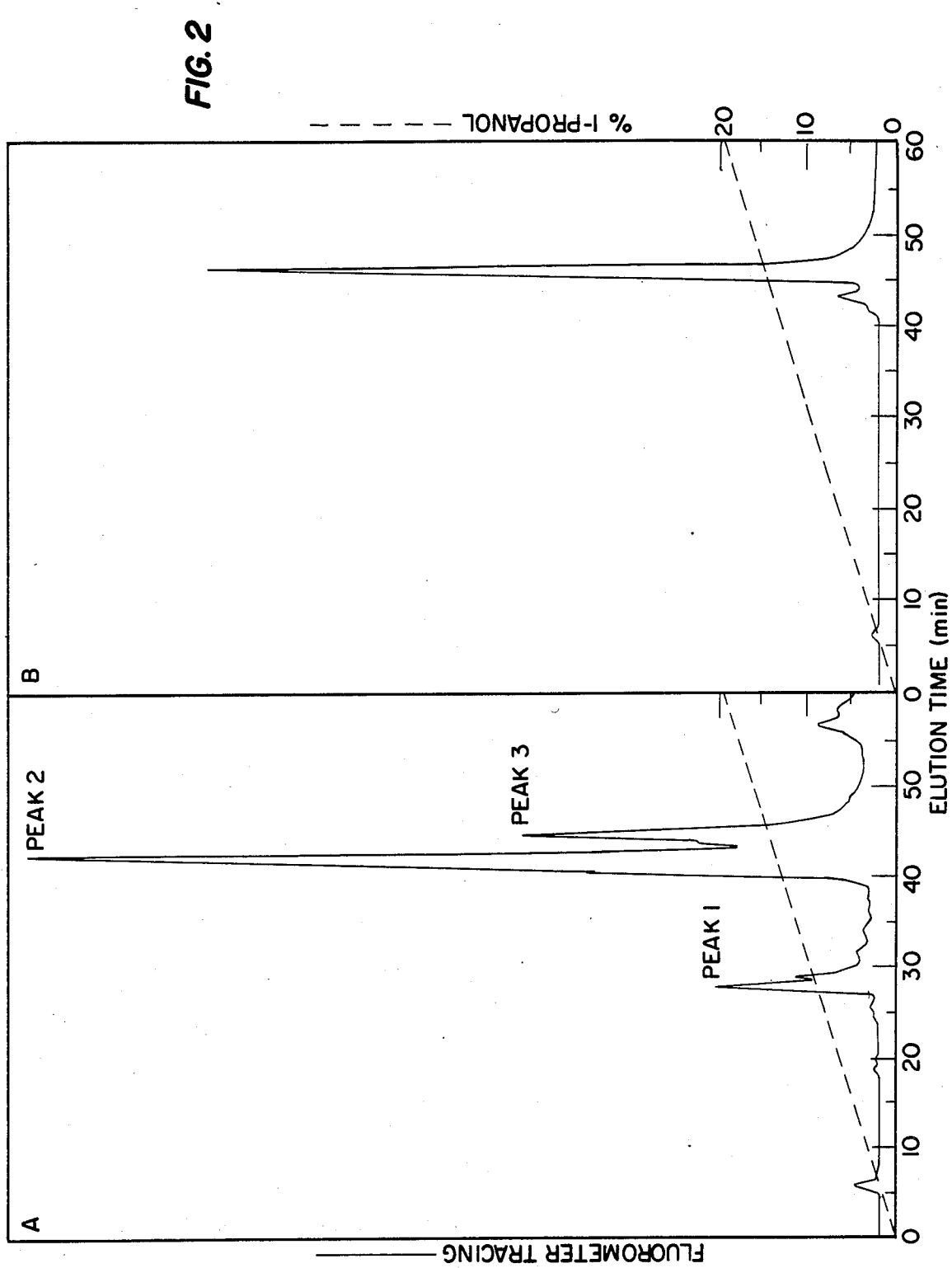

Purification of parathymosin alpha from peak alpha by use of reverse phase HPLC is described below. The fractions comprising peak alpha (pooled as described in the description of FIG. 1 above) were lyophilized and the residue dissolved in 900 μl of buffer A. The HPLC runs were carried out with 150 μl aliquots of this solution. Elution was with a gradient of 0–20% 1-propanol in buffer A as shown in FIG. 2A. Fractions of 0.6 ml were collected. For analysis with fluorescamine, 5 μl aliquots were diverted to the detector every 6 seconds. As shown in FIG. 2 A. fractions 45 and 46 (peak 3) were pooled, combined with similar fractions from 5 other HPLC separations and lyophilized.

The lyophilized peptides from peak 3 (57 μg) were chromatographed on reverse phase HPLC under the same conditions as set forth above. The major protein peak obtained corresponds to essentially pure parathymosin alpha (FIG. 2B).

When the isolation procedure described above was applied to extracts from other rat tissues, such as lung, kidney, liver and brain, the HPLC peak corresponding to parathymosin alpha was found to be much more prominent than the peak containing prothymosin alpha. Amino acid analysis of the peptide in this peak confirmed its identity with parathymosin alpha purified from rat thymus (compare Tables I and II provided below).

TABLE I

| Amino acid composition of parathymosin $\alpha^a$ | | |
|---|---|---|
| | Parathymosin $\alpha$ | Prothymosin $\alpha^b$ |
| Asx | 13.0 ± 0.8 (13) | 25.6 ± 0.8 (26) |
| Thr | 2.8 ± 0.1 (3) | 6.0 ± 0.2 (6) |
| Ser | 3.7 ± 0.2 (4) | 3.2 ± 0.2 (3) |
| Glx | 39.5 ± 1.6 (40) | 39.6 ± 2.7 (40) |
| Gly | 6.5 ± 0.2 (7) | 5.3 ± 0.3 (5) |
| Ala | 10.8 ± 0.5 (11) | 10.3 ± 0.7 (10) |
| Val | 4.5 ± 0.1 (5) | 5.9 ± 0.2 (6) |
| Ile | 0.05 ± 0.01 (0) | 1.0 ± 0.0 (1) |
| Leu | 2.0 ± 0.0 (2) | 1.0 ± 0.0 (1) |
| Lys | 12.5 ± 0.3 (13) | 9.8 ± 0.3 (10) |
| Arg | 4.7 ± 0.1 (5) | 2.3 ± 0.2 (2) |
| Pro | 1.8 ± 0.0 (2) | 2.4 ± 0.6 (2) |
| Total | (105) | (112) |

[a]The values shown are the mean and standard deviations from analyses of six samples of parathymosin α hydrolyzed with redistilled 5.7 M HCl at 150° for 1 hr. The values are calculated assuming two residue of leucine in parathymosin α and one of leucine residues in prothymosin α₁. The nearest integral numbers are shown in parentheses. Tryptophan, cysteine, phenylalanine, tyrosine, histidine and methionine were not detected.
[b]Data from Haritos et al Proc. Natl. Acad. Sci. U.S.A. 81, 1008–1011 (1984).

(a) The values shown are the mean and standard deviations from analyses of six samples of parathymosin α hydrolyzed with redistilled 5.7M HCl at 150° for 1 hr. The values are calculated assuming two residue of leucine in parathymosin α and one of lecine residues in prothymosin α₁. The nearest integral numbers are shown in parentheses. Tryptophan, cysteine, phenylalanine, tyrosine, histidine and methionine were not detected.

(b) Data from Haritos et al Proc. Natl. Acad. Sci. U.S.A. 81, 1008–1011 (1984).

TABLE II

| Residue | Amino acid compositions of parathymosin α from various rat tissues[a] | | | | | |
|---|---|---|---|---|---|---|
| | Thymus | Spleen | Lung | Kidney | Liver | Brain |
| Asx | 13.0 | 13.8 | 13.3 | 14.3 | 13.1 | 13.4 |
| Thr | 2.8 | 3.2 | 3.2 | 3.1 | 2.7 | 2.7 |
| Ser | 3.7 | 3.8 | 3.9 | 3.8 | 3.7 | 3.7 |
| Glu | 39.5 | 38.2 | 42.3 | 41.0 | 38.2 | 37.6 |
| Gly | 6.5 | 7.2 | 6.6 | 6.9 | 6.6 | 7.0 |
| Ala | 10.8 | 9.5 | 8.7 | 10.9 | 10.1 | 10.9 |
| Val | 4.5 | 4.4 | 4.5 | 4.9 | 4.6 | 4.7 |
| Leu | 2.0 | 2.0 | 2.0 | 2.0 | 2.0 | 2.0 |
| Lys | 12.5 | 12.3 | 12.5 | 13.7 | 12.4 | 13.1 |
| Arg | 4.7 | 4.5 | 5.0 | 5.5 | 4.9 | 5.0 |
| Pro[b] | 1.8 | (2)[b] | (2) | (2) | (2) | (2) |

[a]Fractions corresponding to peak 3 from rat thymus (FIG. 2) were pooled and aliquots hydrolyzed with redistilled 5.7 M HCl at 150° C. for 1 h. Amino acid analyses were carried out as described
The values are calculated assuming 2 residues of leucine in parathymosin α.
[b]Not determined. The content of proline in peptides from other tissues was assumed to be 2.

(a) Fractions corresponding to peak 3 from rat thymus (FIG. 2) were pooled and aliquots hydrolyzed with redistilled 5.7M HCl at 150° C. for 1 h. Amino acid analyses were carried out as described The values are calculated assuming 2 residues of leucine in parathymosin α.

(b) Not determined. The content of proline in peptides from other tissues was assumed to be 2.

It is seen from Table I that the amino acid composition of parathymosin alpha was similar to that previously reported for prothymosin alpha. The major differences are a smaller number of Asx residues, a higher content of lysine and arginine, and the absence of isoleucine. The differences in amino acid composition account for the higher isoelectric point of parathymosin alpha (pI equals 4.15) as compared with prothymosin alpha (pI equals 3.5).

The concentration of parathymosin alpha and prothymosin alpha in various rat tissues is summarized below in Table III.

TABLE III

| | Content of parathymosin α and prothymosin α in rat tissues | | | |
|---|---|---|---|---|
| Tissue | Ratio of peak heights[a] | Prothymosin α[b] μg/g tissue | Parathymosin α μg/g tissue | Parathymosin α + prothymosin α μg/g tissue |
| Thymus | 0.38 | 414 | 157 | 571 |
| Spleen | 0.44 | 270 | 119 | 389 |
| Lung | 1.72 | 154 | 265 | 419 |
| Kidney | 2.50 | 126 | 315 | 441 |
| Liver | 4.80 | 68 | 326 | 394 |
| Brain | 3.57 | 58 | 207 | 265 |

[a]Estimated from the results of HPLC.
[b]Based on radioimmune assay of extracts of boiled tissue.
See Haritos et al., Proc. Natl. Acad. Sci. U.S.A. 81, 1391–1393 (1984).

Concentrations of parathymosin alpha in the various indicated rat tissues were estimated from the relative peak heights of peaks 2 and 3 after separation by HPLC and the known quantities of prothymosin alpha in the crude tissue extracts, which were determined by a radioimmunoassay using purified prothymosin alpha as the reference standard. In contrast to thymus and spleen, where prothymosin alpha was the major peptide, the concentration of parathymosin alpha was found to be highest in rat liver, followed by kidney, lung and brain. The reciprocal relationship of prothymosin alpha and parathymosin alpha resulted in the relatively constant values for the sum of the concentrations of the two peptides. The low value for the total estimated for brain may be due to uncertainty in the calculation based on the low recovery of prothymosin alpha in the HPLC separations.

Figure 3:
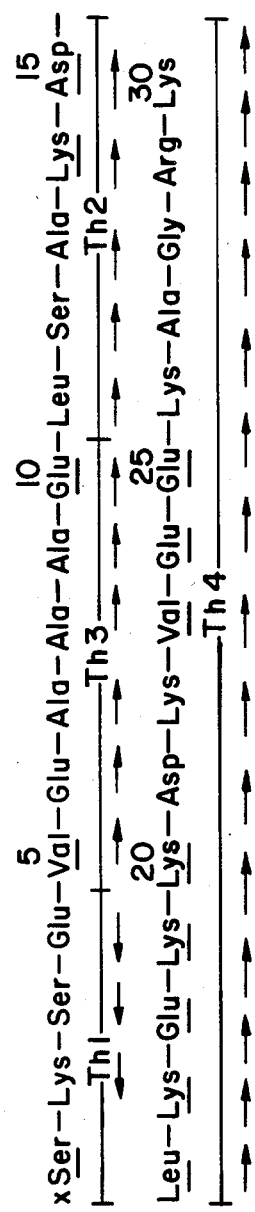

Additional characterization of the parathymosin alpha molecule was obtained by carrying out automated sequence analysis. Due to observed blocking group on the amino terminus of parathymosin alpha, the sequence of the first 30 amino acid residues was deduced from the amino acid composition and sequence analysis of peptides obtained by digestion with thermolysin. Identity with prothymosin alpha was found at positions 1, 5, 10, 14–20 and 23–25, accounting for 13 of the first 30 residues from the amino-terminus. The amino acid sequence of the amino-terminal region of parathymosin alpha is shown in FIG. 3 with X representing the undetermined blocking group. The peptides obtained by digestion with thermolysin (Th1–Th4) were separated by HPLC using conditions described previously in the purification. In FIG. 3 the sequence is deduced from results of automated sequence analysis (→) or digestion with carboxypeptidase A (←) as shown. The underlined residues in this Figure are those which are identical to those in prothymosin alpha.

The fractions containing parathymosin alpha fail to show significant activity in a radioimmunoassay for thymosin alpha-1. This is attributed to the differences in amino acid sequence at the amino-terminus since the major epitope for the antiserum employed as derived from the amino-terminal sequence. The cellular functions of prothymosin alpha and parathymosin alpha remained unknown. However, in a mouse protection test of Salvin and Neta, Cell Immunol. 75, 160 (1983) previously employed to evaluate the immuno-enhancing properties of thymosin alpha-1 and thymosin alpha-11 as reported by Caldarella et al., Proc. Natl. Acad. Sci. U.S.A. 80, 7424 (1983), prothymosin alpha was found to be active at doses significantly lower than those reported for the smaller peptide fragments, suggesting that its activity was not due to the formation of these fragments. In this mouse protection test, parathymosin alpha exhibited much weaker activity, but most significantly when it was administered together with prothymosin alpha, it appeared to neutralize or block the effects of the latter. The data of such comparative testing is summarized below in Table IV.

TABLE IV

Effects of prothymosin α and parathymosin α on the growth of *Candida albicans* in C₃H/HeJ mice

| Peptide and dose administered[a] | | *C. albicans* cell count[b] | |
|---|---|---|---|
| Prothymosin α ng | Parathymosin α ng | 12th day after challenge | 14th day after challenge |
| 0 | 0 | 3740 | 6670 |
| 80 | 0 | 0 | 160 |
| 160 | 0 | 1 | 16 |
| 320 | 0 | 1 | 1 |
| 0 | 80 | 1570 | 2570 |
| 0 | 160 | 5040 | 2990 |
| 0 | 320 | 4270 | 3510 |
| 160 | 160 | 820 | 3860 |

[a]Mice were treated daily with the indicated doses of prothymosin α or parathymosin α, or with both peptides as indicated. Two days after the start of treatment the mice were challenged with 4 × 10⁴ cell of *C. albicans* (Salvin, S.B. and Neta, R., Cell. Immunol. 75,160-172 (1983)) (Caldarella, J. et al. Proc. Natl. Acad. Sci. U.S.A. 80, 7424-7427 (1983)).
[b]Three mice from each set were sacrificed on days 12 and 14 after infection. The values represent the average number of organisms in the left kidneys of the mice in each set.

(a) Mice were treated daily with the indicated doses of prothymosin α or parathymosin α, or with both peptides as indicated. Two days after the start of treatment the mice were challenged with 4×10⁴ cell of *C. albicans* (Salvin, S. B. and Neta, R., Cell. Immunol. 75, 160–172 (1983)) (Caldarella, J. et al. Proc. Natl. Acad. Sci. U.S.A. 80, 7424–7427 (1983)).

(b) Three mice from each set were sacrificed on days 12 and 14 after infection. The values represent the average number of organisms in the left kidneys of the mice in each set.

Thus parathymosin alpha can be utilized as an immuno-modulating agent and may be utilized in subjects whose immune system is improperly potentiated such as in auto-immune diseases. Alternatively, the modulating action of this parathymosin alpha compound can be employed in modulating the immune status of patients who require immune suppression such as subjects undergoing tissue or organ transplantation.

Parathymosin alpha can be conveniently administered in conventional parenteral dosage forms suitable for injection. It can be employed as a lyophilized solid, e.g. 1 mg which can be reconstituted prior to use by addition of sterile water for injection. Suitable dosage regimens will of course depend upon the nature of the therapy desired i.e. immuno modulation to reduce a potentiated immune system or to suppress a normal immune system. Suitable dosage regimens include a daily dosage of from 1 to 100 μg/kg per day given iv, im or sc. The parenteral dosage form can include suitable conventional adjuvants such as for example carrier proteins, e.g. human serum albumin USP, buffers, preservatives and the like.

Also included within the scope of the present invention are the pharmaceutically acceptable salts of prothymosin α such as the sodium or potassium salts or salts with strong organic bases such as guanidine. In addition, the counterions of these cations as well as the lysine residues in parathymosin alpha, such as the hydrochloride, hydrobromide, sulfate, phosphate, maleate, acetate, citrate, benzoate, succinate, ascorbate and the like, may be included in the preparation.

I claim:

1. A peptide of about 105 amino acids having a pI of about 4.15, a partial amino acid sequence at the amino-terminal as follows: X-Ser-Lys-Ser-Glu-Val-Glu-Ala-Ala-Ala-Glu-Leu-Ser-Ala-Lys-Asp-Leu-Lys-Glu-Lys-Lys-Asp-Lys-Val-Glu-Glu-Lys-Ala-Gly-Arg-Lyswherein X is a blocking group; said peptide having an amino acid composition as follows:

| Asx | 13.0 ± 0.8 | (13) | Arg. | 4.7 ± 0.1 | (5) |
|---|---|---|---|---|---|
| Thr | 2.8 ± 0.1 | (3) | Pro | 1.8 ± 0.0 | (2) |
| Ser | 3.7 ± 0.2 | (4) | Total | (105) | |
| Glx | 39.5 ± 1.6 | (40) | | | |
| Gly | 6.5 ± 0.2 | (7) | | | |
| Ala | 10.8 ± 0.5 | (11) | | | |
| Val | 4.5 ± 0.1 | (5) | | | |
| Ile | 0.05 ± 0.01 | (0) | | | |
| Leu | 2.0 ± 0.0 | (2) | | | |
| Lys | 12.5 ± 0.3 | (13) | | | |

2. A pharmaceutical composition comprising an immuno-modulating effective amount of the peptide of claim 1 and a conventional pharmaceutical parenteral carrier material.

3. A method for modulating immune response in an animal comprising administering to said animal an immuno-modulating effective amount of a peptide of about 105 amino acids having a pI of about 4.15, a partial amino acid sequence at the amino terminal as follows:

X-Ser-Lys-Ser-Glu-Val-Glu-Ala-Ala-Ala-Glu-Leu-Ser-Ala-Lys-Asp-Leu-Lys-Glu-Lys-Lys-Asp-Lys-Val-Glu-Glu-Lys-Ala-Gly-Arg-Lys-

Wherein X is a blocking group; said peptide having an amino acid composition as follows:

| Asx | 13.0 ± 0.8 | (13) | Arg. | 4.7 ± 0.1 | (5) |
|---|---|---|---|---|---|
| Thr | 2.8 ± 0.1 | (3) | Pro. | 1.8 ± 0.0 | (2) |
| Ser | 3.7 ± 0.2 | (4) | Total | (105) | |
| Glx | 39.5 ± 1.6 | (40) | | | |
| Gly | 6.5 ± 0.2 | (7) | | | |
| Ala | 10.8 ± 0.5 | (11) | | | |
| Val | 4.5 ± 0.1 | (5) | | | |
| Ile | 0.05 ± 0.01 | (0) | | | |
| Leu | 2.0 ± 0 | (2) | | | |
| Lys | 12.5 ± 3 | (13) | | | |

4. The method of claim 3 wherein a daily dosage in the range of from about 1 to 100 mcg/kg of body weight is administered.

* * * * *